United States Patent [19]

Lunkenheimer et al.

[11] Patent Number: 4,782,086

[45] Date of Patent: Nov. 1, 1988

[54] E-ISOMERS OF $N^{\alpha}$-(2-CYANO-2-ALKOXIMINOACETYL)-AMINO ACID DERIVATIVES, COMPOSITIONS AND FUNGICIDAL USE

[75] Inventors: Winfried Lunkenheimer, Wuppertal; Hans Scheinpflug, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 17,297

[22] Filed: Feb. 20, 1987

Related U.S. Application Data

[63] Continuation-in-part of Ser. No. 868,844, May 29, 1986, abandoned.

[30] Foreign Application Priority Data

Jun. 13, 1985 [DE] Fed. Rep. of Germany ....... 3521131
Jan. 25, 1986 [DE] Fed. Rep. of Germany ....... 3602243

[51] Int. Cl.$^4$ ..................... A01N 37/34; A01N 37/46; C07C 131/00; C07D 295/18

[52] U.S. Cl. .................................... 514/521; 544/364; 544/366; 544/370; 544/371; 544/372; 544/386; 544/391; 544/130; 544/134; 544/139; 544/140; 544/141; 544/159; 544/163; 544/360; 546/187; 546/189; 546/208; 546/210; 546/211; 546/226; 548/262; 548/336; 548/342; 548/374; 548/378; 548/524; 548/540; 548/301; 514/235.5; 514/235.8; 514/236.2; 514/236.5; 514/237.5; 514/252; 514/255; 514/316; 514/326; 514/330; 514/383; 514/397; 514/400; 514/406; 514/422; 514/423; 514/522; 514/528

[58] Field of Search ............... 544/130, 364, 134, 366, 544/139, 370, 140, 371, 141, 372, 159, 386, 163, 341, 360; 546/187, 210, 189, 211, 208, 226; 548/262, 378, 336, 524, 342, 540, 374; 558/301; 514/228, 397, 232, 400, 234, 406, 252, 422, 255, 423, 316, 521, 522, 326, 330, 528, 383, 235.5, 235.8, 236.2, 236.5, 237.5

[56] References Cited

U.S. PATENT DOCUMENTS 4,178,383 12/1979 Brandes et al. ..................... 558/301

FOREIGN PATENT DOCUMENTS 2173791 10/1986 United Kingdom .

*Primary Examiner*—Robert W. Ramsuer
*Attorney, Agent, or Firm*—Sprung Horn Kramer & Woods

[57] ABSTRACT

Fungicidally active novel E-isomers of $N^{\alpha}$-(2-cyano-2-alkoximino-acetyl)-amino acid derivatives and peptides of the general formula (I)

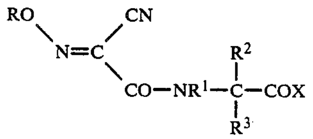

(I)

in which

R represents alkyl, alkenyl, alkinyl, cyanoalkyl, azolylalkyl or optionally substituted phenylalkyl, or represents optionally substituted cycloalkyl;

$R^1$ represents hydrogen, alkyl, optionally substituted phenyl or optionally substituted benzyl, or represents alkoxycarbonylamino;

$R^2$ represents hydrogen or alkyl;

$R^3$ represents hydrogen, alkyl, alkoxycarbonylalkyl, hydroxycarbonylalkyl, aminocarbonylalkyl, azolylalkyl, cyanoalkyl, hydroxyalkyl, alkenyl, alkinyl or optionally substituted cycloalkyl, or represents optionally substituted phenyl or phenylalkyl, or represents the grouping $R^4$—$SO_n$—Z—

$R^4$ n and Z having various meanings, and
X is —OH—$OR^1$ or —$NR^2R^3$.

13 Claims, No Drawings

E-ISOMERS OF $N^{\alpha}$-(2-CYANO-2-ALKOXIMINOACETYL)-AMINO ACID DERIVATIVES, COMPOSITIONS AND FUNGICIDAL USE This is a continuation-in-part of Application Ser. No. 868,844, filed May 29, 1986, now abandoned.

The present invention relates to new E-isomers of Nα-(2-cyano-2-alkoximinoacetyl)-amino acid derivatives and peptides, several processes for their preparation and their use as agents for combating pests, in particular as fungicides.

It is already known that certain compounds, such as, for example, N-trichloromethylthio-tetrahydrophthalimide, zinc ethylene-1,2-bis-dithiocarbamate and N-ethylaminocarbonyl-2-cyano-2-methoximino-acetamide, have a good fungicidal activity (compare, for example, U.S. Pat. No. 2,553,770, U.S. Pat. No. 2,457,674 and DE-OS (German Published Specification) No. 2,312,956). However, the action of these compounds is not always completely satisfactory, especially when low amounts and concentrations are applied.

New E-isomers of Nα-(2-cyano-2-alkoximino-acetyl-)amino acid derivatives and peptides of the general formula (I)

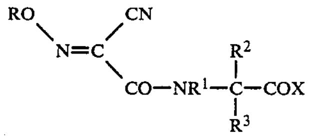

(I)

in which

R represents alkyl, alkenyl, alkinyl, cyanoalkyl, azolyalkyl or optionally substituted phenylalkyl, or represents optionally substituted cycloalkyl;

$R^1$ represents hydrogen, alkyl, optionally substituted phenyl or optionally substituted benzyl, or represents alkoxycarbonylamino;

$R^2$ represents hydrogen or alkyl;

$R^3$ represents hydrogen, alkyl, alkoxycarbonylalkyl, hydroxycarbonylalkyl, aminocarbonylalkyl, azolylalkyl, cyanoalkyl, hydroxyalkyl, alkenyl, alkinyl or optionally substitued cycloalkyl, or represents optionally substituted phenyl or phenylalkyl, or represents the grouping $R^4—SO_n—Z—$ wherein $R^4$ represents hydrogen, alkyl or optionally substituted phenylalkyl;

n represents the numbers 0, 1 or 2 and

Z represents a straight-chain or branched alkylene chain; or $R^1$ and $R^3$, together with the nitrogen atom and the carbon atom to which they are bonded, represent a 5- or 6-membered heterocyclic ring; or $R^2$ and $R^3$, together with the carbon atom to which they are bonded, represent cycloalkylidene and X represents the grouping $—OR^I$ or $NR^{II}R^{III}$, wherein $R^I$ represents hydrogen, alkyl or alkenyl, or represents alkinyl;

$R^{II}$ represents hydrogen or alkyl;

$R^{III}$ represents hydrogen, alkyl, alkenyl, alkinyl, halogenoalkyl, alkoxyalkyl, dialkylaminoalkyl, alkoxycarbonylalkyl, hydroxycarbonylalkyl, aminocarbonylalkyl, alkylaminocarbonylalkyl, dialkylaminocarbonylalkyl, cyanoalkyl, optionally substituted phenylalkyl, optionally substituted phenyl or optionally substituted cycloalkyl, or represents an acylamino radical, or represents the grouping $—N=CH—R^{IV}$ wherein $R^{IV}$ represents alkyl or optionally substituted phenyl, or $R^{II}$ and $R^{III}$, together with the nitrogen atom to which they are bonded, represent an optionally substituted heterocyclic ring, which can contain further hetero atoms, and physiologically acceptable optionally substituted ammonium, alkali metal and alkaline earth metal salts and metal salt complexes thereof.

In the case where $R^2$ and $R^3$ have a different meaning, the compounds of the formula (I) have an asymmetric carbon atom; they can thus also be in the form of optical isomers (D- and L-configuration), which can be obtained in various proportions. They are predominantly obtained as racemates.

It has furthermore been found that the E-isomers of Nα-(2-cyano-2-alkoximinoacetyl)-amino acid derivatives and peptides of the formula (I)

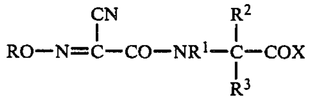

(I)

in which

R represents alkyl, alkenyl, alkinyl, cyanoalkyl, azolylalkyl or optionally substitued phenylalkyl, or represents optionally substituted cycloalkyl;

$R^1$ represents hydrogen, alkyl, optionally substituted phenyl or optionally substituted benzyl, or represents alkoxycarbonylamino;

$R^2$ represents hydrogen or alkyl;

$R^3$ represents hydrogen, alkyl, alkoxycarbonylalkyl, hydroxycarbonylalkyl, aminocarbonylalkyl, azolylalkyl, cyanoalkyl, hydroxyalkyl, alkenyl, alkinyl or optionally substituted cycloalkyl, or represents optionally substituted phenyl or phenylalkyl, or represents the grouping $R^4—SO_n—Z—$ wherein $R^4$ represents hydrogen, alkyl or optionally substituted phenylalkyl;

n represents the numbers 0, 1 or 2 and

Z represents a straight-chain or branched alkylene chain; or $R^1$ and $R^3$, together with the nitrogen atom and the carbon atom to which they are bonded, represent a 5- or 6-membered heterocyclic ring; or $R^2$ and $R^3$, together with the carbon atom to which they are bonded, represent cycloalkylidene and X represents the grouping $OR^I$ or $NR^{II}R^{III}$, wherein $R^1$ represents hydrogen, alkyl or alkenyl, or represents alkinyl;

$R^{II}$ represents hydrogen or alkyl;

$R^{III}$ represents hydrogen, alkyl, alkenyl, alkinyl, halogenoalkyl, alkoxyalkyl, dialkylaminoalkyl, alkoxycarbonylalkyl, hydroxycarbonylalkyl, aminocarbonylalkyl, alkylaminocarbonylalkyl, dialkylaminocarbonylalkyl, cyanoalkyl, optionally substituted phenylalkyl, optionally substituted phenyl or optionally substituted cycloalkyl, or represents an acylamino radical, or represents the grouping $$—N=CH—R^{IV}$$

wherein $R^{IV}$ represents alkyl or optionally substituted phenyl, or $R^{II}$ and $R^{III}$, together with the nitrogen atom to which they are bonded, represent an optionally substituted heterocyclic ring, which can contain further hetero atoms, and physiologically acceptable optionally substituted ammonium, alkali metal and alkaline earth metal salts and metal salt complexes thereof are obtained by a process in which (a) amino acid derivatives of the formula (II)

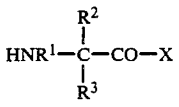
(II)

in which $R^1$, $R^2$, $R^3$ and X have the abovementioned meanings, are reacted with carboxyl-activated derivatives of the E-isomers of the carboxylic acids of the formula (III)

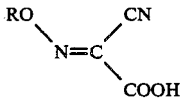
(III)

in which

R has the abovementioned meaning, if appropriate in the presence of a catalyst, if appropriate in the presence of an acid-binding agent and if appropriate in the presence of a diluent, or (b) carboxyl-activated derivatives of the E-isomers of carboxylic acids of the formula (III)

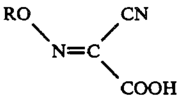
(III)

in which R has the abovementioned meaning, are reacted first with amines of the formula (IV)

$$H_2NR^1 \quad (IV)$$

in which $R^1$ has the abovementioned meaning, and then with carbonyl derivatives of the formula (V)

$$R^2—CO—R^3 \quad (V)$$

in which $R^2$ and $R^3$ have the abovementioned meanings, and finally with isonitriles of the formula (VI)

$$CN—R^5 \quad (VI)$$

in which $R^5$ represents alkyl, alkenyl, alkinyl, cyanoalkyl or alkoxycarbonylalkyl, or represents optionally substituted cycloalkyl, phenyl or phenylalkyl, if appropriate in the presence of a diluent, or (c) carboxyl-activated derivatives of the E-isomers of amino acids of the formula (Ia)

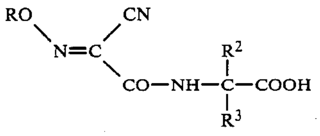
(Ia)

in which R, $R^2$ and $R^3$ have the abovementioned meanings, are reacted with amines of the formula (VII)

$$H—NR^{II}R^{III} \quad (VII)$$

in which $R^{II}$ and $R^{III}$ have the abovementioned meanings, if appropriate in the presence of a catalyst and if appropriate in the presence of an acid-binding agent and if appropriate in the presence of a diluent, or (d) E-isomers of amino acid derivatives of the formula (Ib)

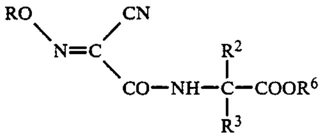
(Ib)

in which

R, $R^2$ and $R^3$ have the abovementioned meanings and $R^6$ represents alkyl with 1 to 4 carbon atoms, are reacted with amines of the formula (VII)

$$H—NR^{II}R^{III} \quad (VII)$$

in which $R^{II}$ and $R^{III}$ have the abovementioned meanings, if appropriate in the presence of a diluent.

The compounds of the formula (I) which are thus to be obtained and in which X represents a hydroxyl group can form salts with amines and alkali metal or alkaline earth metal hydroxides, carbonates or bicarbonates, as well as ammonium hydroxide—they can furthermore form metal complexes with heavy metal salts.

Finally, it has been found that the new E-isomers of Nα-(2-cyano-2-alkoximinoacetly)-amino acid derivatives and peptides of the formula (I) and optionally substituted ammonium, alkali metal and alkaline earth metal salts and metal salt complexes thereof have, in particular, powerful fungicidal properties. Surprisingly, the compounds according to the invention thereby exhibit a more powerful action than the compounds known from the prior art, such as N-trichloromethylthio-tetrahydrophthalimide, zinc ethylene-1,2-bis-dithiocarbamate and N-ethylaminocarbonyl-2-cyano-2-methoximinoacetamide, which are closely related compounds structurally or from the point of view of their action. The substances according to the invention thus represent an enrichment of the art.

Formula (I) provides a general definition of the E-isomers of Nα-(2cyano-2-alkoximinoacetyl)-amino acid derivatives and peptides according to the invention. Preferred compounds of the formula (I) are those in which R represents straight-chain or branched alkyl with 1 to 8 carbon atoms or alkenyl or alkinyl with in each case 2 to 4 carbon atoms, cyanoalkyl with 1 to 4 carbon atoms, 1,2,4-triazol-1-yl-alkyl or pyrazol-1-yl-alkyl with 1 to 6 carbon atoms in the alkyl part in each case, or represents phenylalkyl which has 1 to 4 carbon atoms in the alkyl part and is optionally mono-, di- or trisubstituted in the phenyl part by identical or different substituents, preferred substituents which may be mentioned being: halogen, cyano, nitro, hydroxyl, alkyl, alkoxy, alkylthio, alkylsulfinyl and alkylsulfonyl with in each case 1 to 4 carbon atoms and phenyl which is optionally mono-, di- or trisubstituted by identical different halogen substituents; or represents cycloalkyl which has 3 to 7 carbon atoms and is optionally mono-, di- or trisubstituted by identical or different substitutents, preferred substituents which may be mentioned being halogen and alkyl with 1 to 4 carbon atoms;

$R^1$ represents hydrogen or straight-chain or branched alkyl with 1 to 4 carbon atoms, or represents phenyl or benzyl, in each case optionally mono-, di- or trisubstituted by identical or different substituents, preferred possible substituents being the phenyl substituents already mentioned for R, or represents alkoxycarbonylamino with 1 to 4 carbon atoms in the alkyl part, $R^2$ represents hydrogen or straight-chain or branched alkyl with 1 to 4 carbon atoms;

$R^3$ represents hydrogen or straight-chain or branched alkyl with 1 to 6 carbon atoms, or represents straight-chain or branched hydroxyalkyl with 1 to 4 carbon atoms, alkoxycarbonylalkyl with 1 to 4 carbon atoms in each alkyl part and alkoxy part respectively, hydroxycarbonylalkyl and aminocarbonylalkyl with 1 to 4 carbon atoms in each alkyl part, 1,2,4-triazol-1-yl-alkyl, 1,2,4-triazolyl-4-yl-alkyl, imidazol-4-yl-alkyl and pyrazol-1-yl-alkyl with 1 to 6 carbon atoms in the alkyl part in each case, cyanoalkyl with 1 to 4 carbon atoms in the alkyl part, or represents alkenyl or alkinyl with in each case 2 to 4 carbon atoms, or represents cycloalkyl which has 3 to 7 carbon atoms and is optionally mono-, di- or trisubstituted by identical or different substituents, preferred substituents which may be mentioned being halogen and alkyl with 1 to 4 carbon atoms, or furthermore represents phenyl or phenylalkyl, with 1 to 4 carbon atoms in the alkyl part, optionally mono-, di- or trisubstituted in the phenyl part by identical or different substituents, preferred possible substituents in each case being phenyl substituents already mentioned for R, or represents the grouping $R^4—SO_n—Z—$ wherein $R^4$ represents hydrogen, or represents straight-chain or branched alkyl with 1 to 4 carbon atoms, or represents phenylalkyl which has 1 to 4 carbon atoms in the alkyl part and is optionally mono-, di- or trisubstituted in the phenyl part by identical or different substituents, possible substituents being the phenyl substituents already mentioned for R, n represents the number 0, 1 or 2 and Z represents a straight-chain or branched alkylene chain with 1 to 4 carbon atoms; or $R^1$ and $R^3$, together with the nitrogen atom and the carbon atom to which they are bonded, represent a 5 or 6 membered heterocyclic ring; or $R^2$ and $R^3$, together with the carbon atom to which they are bonded, represent cycloalkylidene with 3 to 6 carbon atoms;

X represents the groupings $—OR^I$ or $—NR^{II}R^{III}$, wherein $R^I$ represents hydrogen or straight-chain or branched alkyl with 1 to 4 carbon atoms or alkenyl or alkinyl with in each case 2 to 4 carbon atoms;

$R^{II}$ represents hydrogen or straight-chain or branched alkyl with 1 to 4 carbon atoms; and $R^{III}$ represents hydrogen or straight-chain or branched alkyl with 1 to 4 carbon atoms, or represents alkenyl or alkinyl with in each case 2 to 4 carbon atoms, or halogenoalkyl with 1 to 4 carbon atoms and 1 to 5 same or different halogeno atoms, or alkoxyalkyl with 1 to 4 carbon atoms in the alkoxy and in the alkyl part, or dialkylaminoalkyl with up to 4 carbon atoms in each alkyl part, or represents alkoxycarbonylalkyl with in each case 1 to 4 carbon atoms in the alkoxy part and in the alkyl part, hydroxycarbonylalkyl with 1 to 4 carbon atoms in the alkyl part or aminocarbonylalkyl, alkylaminocarbonylalkyl or dialkylaminocarbonylalkyl with in each case 1 to 4 carbon atoms in each alkyl part or represents cyanoalkyl with 1 to 4 carbon atoms in the alkyl part, phenylalkyl which has 1 to 4 carbon atoms in the alkyl part and is optionally mono-, or di- or trisubstituted in the phenyl part by identical or different substituents or phenyl which is mono-, di- or trisubstituted by identical or different substituents, possible substituents in each case being the phenyl substituents already mentioned for R, or represents cycloalkyl which has 3 to 7 carbon atoms and is optionally substituted by identical or different substituents, preferred possible substituents being halogen and alkyl with 1 to 4 carbon atoms, or represents alkylcarbonylamino or alkoxycarbonylamino with in each case 1 to 4 carbon atoms in the alkyl part or in the alkoxy part, or furthermore represents aminocarbonylamino, alkylaminocarbonylamino or dialkylaminocarbonylamino with 1 to 4 carbon atoms in each alkyl part and in each case, or formylamino, or represents the grouping $—N=CH—R^{IV}$ $R^{IV}$ represents straight-chain or branched alkyl with 1 to 4 carbon atoms or phenyl which is optionally mono-, di- or trisubstituted by identical or different substituents, possible substituents being the phenyl substituents already mentioned for R, or $R^{II}$ and $R^{III}$, together with the nitrogen atom to which they are bonded, represent a 5- or 6-membered heterocyclic ring, which can optionally contain oxygen or nitrogen as further hetero atoms and can be optionally substituted by cyano, halogen, alkyl with 1 to 4 carbon atoms, hydroxycarbonyl, alkoxycarbonyl with 1 to 4 carbon atoms in the alkoxy part, aminocarbonyl, alkylaminocarbonyl and dialkylaminocarbonyl with 1 to 4 carbon atoms in each alkyl part in each case.

Particularly preferred compounds of the formula (I) are those in which

R represents straight-chain or branched alkyl with 1 to 4 carbon atoms, allyl or propargyl, cyanomethyl, cyanoethyl, 1,2,4-triazol-1-yl-alkyl or pyrazol-1-yl-alkyl with 1 to 4 carbon atoms in the alkyl part in each case, or represents phenylalkyl which has 1 to 2 carbon atoms in the alkyl part and is optionally mono- or disubstituted in the phenyl part by identical or different substituents, substituents which may be mentioned in particular being: fluorine, chlorine, cyano, nitro, hydroxyl, methyl, methoxy, methylthio, methylsulfinyl, methylsulfonyl and phenyl which is optionally mono- or disubstituted by identical or different substituents from the group comprising fluorine and chlorine; or furthermore represents cyclopropyl, cyclobutyl, cyclopentyl, cyclohexyl or cycloheptyl, in each case optionally mono- or disubstituted by identical or different substituents from the group comprising fluorine, chlorine and methyl;

$R^1$ represents hydrogen, methyl or ethyl, or represents phenyl or benzyl, in each case optionally mono- or disubstituted by identical or different substituents, possible substituents being, in particular, the phenyl substituents already mentioned for R; or furthermore represents methoxycarbonylamino or ethoxycarbonylamino;

$R^2$ represents hydrogen, methyl or ethyl;

$R^3$ represents hydrogen, straight-chain or branched alkyl with 1 to 4 carbon atoms, hydroxymethyl or 1-hydroxyethyl, methoxycarbonylmethyl, methoxycarbonylethyl, ethoxycarbonylmethyl, ethoxycarbonylethyl, hydroxycarbonylmethyl, hydroxycarbonylethyl, aminocarbonylmethyl, aminocarbonylethyl, 1,2,4-triazol-1-yl-alkyl, 1,2,4-triazol-4-yl-alkyl, imidazol-4-yl-alkyl and pyrazol-1-yl-alkyl with 1 to 4 carbon atoms in each alkyl part in each case, cyanomethyl, cyanoethyl, or represents allyl, or represents propargyl, or represents or cyclopropyl, cyclobutyl, cyclopentyl, cyclohexyl or cycloheptyl, in each case optionally mono- or disubstituted by identical or different substituents from the group comprising fluorine, chlorine and methyl; or furthermore represents phenylalkyl which has 1 to 2 carbon atoms in the alkyl part and is optionally mono- or disubstituted in the phenyl part by identical or different substituents, or phenyl which is mono- or disubstituted by identical or different substituents, possible substituents being the phenyl substituents already mentioned for R, or furthermore represents the grouping $$R^4—SO_n—Z—$$

wherein $R^4$ represents hydrogen, methyl or ethyl, or represents phenylalkyl which has 1 to 2 carbon atoms in the alkyl part and is optionally mono- or disubstituted in the phenyl part by identical or different substituents, possible substituents being, in particular, the phenyl substituents already mentioned for R, n represents the number 0, 1 or 2 and Z represents a straight-chain or branched alkylene chain with 1 to 2 carbon atoms; or $R^1$ and $R^3$, together with the nitrogen atom and the carbon atom to which they are bonded, represent a 5- to 6-membered heterocyclic ring;

$R^2$ and $R^3$, together with the carbon atom to which they are bonded, represent cyclopropylidene, and X represents the groupings $—OR^I$ or $—NR^{II}R^{III}$, wherein $R^I$ represents hydrogen, methyl, ethyl, allyl or propargyl;

$R^{II}$ represents hydrogen, methyl or ethyl;

$R^{III}$ represents hydrogen, methyl, ethyl, n-propyl, isopropyl, n-butyl, iso-butyl, sec.-butyl, tert.-butyl, allyl or propargyl, halogenoalkyl with 1 to 2 carbon atoms and 1 to 3 same or different halogen atoms, for example fluoro and chloro, alkoxyalkyl with each 1 to 2 carbon atoms in the alkoxy and alkyl part, dialkylaminoalkyl with 1 or 2 carbon atoms in each alkyl part, or represents alkoxycarbonylalkyl, hydroxycarbonylalkyl, aminocarbonylalkyl, alkylaminocarbonylalkyl or dialkylaminocarbonylalkyl with in each case 1 or 2 carbon atoms in each alkyl part, or cyanoalkyl; or furthermore represents phenylalkyl which has 1 or 2 carbon atoms in the alkyl part and is optionally mono- or disubstituted in the phenyl part by identical or different substituents or represents phenyl which is mono- or disubstituted by identical or different substituents, possible substituents being in each case the phenyl substituents already mentioned for R; or represents cyclopropyl, cyclobutyl, cyclopentyl, cyclohexyl or cycloheptyl, in each case optionally mono- or disubstituted by identical or different substituents from the group comprising fluorine, chlorine and methyl, or represents alkylcarbonylamino or alkoxycarbonylamino with in each case 1 or 2 carbon atoms in the alkyl part or in the alkoxy part, or represents aminocarbonylamino, methylaminocarbonylamino, ethylaminocarbonylamino, dimethylaminocarbonylamino, diethylaminocarbonylamino, methylethylaminocarbonylamino or formylamino, or represents the grouping $$—N{=}CH—R^{IV}$$

wherein $R^{IV}$ represents methyl or ethyl, or represents phenyl which is optionally mono- or disubstituted by identical or different substituents, possible substituents being the phenyl substitutents already mentioned as preferred for R; or $R^{II}$ and $R^{III}$, together with the nitrogen atom to which they are bonded, represent a 5- or 6-membered heterocyclic ring, which can optionally contain oxygen or nitrogen as further hetero atoms and can optionally substituted by cyano, fluorine, chlorine, bromine, iodine, methyl, ethyl, i-propyl, hydroxycarbonyl, methoxycarbonyl, ethoxycarbonyl, aminocarbonyl, methylaminocarbonyl, ethylaminocarbonyl, dimethylaminocarbonyl, diethylaminocarbonyl and methylethylaminocarbonyl.

The alkali metal, alkaline earth metal and optionally substituted ammonium salts of the E-isomers of those $N^{\alpha}$-(2-cyano-2-alkoximinoacetyl)-amino acid and peptide derivatives of the formula (I) in which X represents a hydroxyl group and R, $R^1$, $R^2$ and $R^3$ have the meanings which have already been mentioned for these substituents are also preferred compounds according to the invention.

Alkali metal and alkaline earth metal hydroxides, carbonates or bicarbonates or amines and ammonium hydroxide can be used for this salt formation. These include, preferably, sodium hydroxide, sodium carbonate, sodium bicarbonate, potassium hydroxide, potassium carbonate, calcium hydroxide and barium hydroxide; ammonia; primary amines, such as methylamine and isopropylamine; secondary amines, such as dimethylamine and dicyclohexylamine; tertiary amines, such as triethylamine, pyridine and N,N-dimethylbenzylamine, and ammonium hydroxides, such as benzyltrimethylammonium hydroxide.

Addition products of salts of metals of main group II to IV and of subgroup I and II and IV to VIII and of those substituted $N^{\alpha}$-(2-cyano-alkoxaminoacetyl)-amino acid and peptide derivatives of the formula (I) in which the substituents R, $R^1$, $R^2$, $R^3$ and X have the meanings which have already been mentioned for these substituents are also preferred compounds according to the invention.

Salts of copper, zinc, manganese, magnesium, tin, iron and nickel are particularly preferred here. Possible anions of these salts are those which are derived from acids which lead to physiologically acceptable addition products. Particularly preferred acids of this type in this connection are the hydrogen halide acids, such as, for example, hydrochloric acid and hydrobromic acid, and furthermore phosphoric acid, nitric acid and sulphuric acid.

If, for example, glycine ethyl ester and 2-cyano-2-methoximino-acetyl chloride are used as starting substances, the course of process (a) according to the invention can be represented by the following equation:

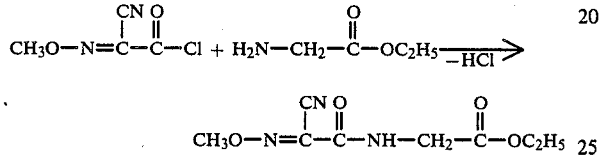

If, for example, 2-cyano-2-methoximinoacetic acid, benzylamine, isobutyraldehyde and ethyl isocyanoacetate are used as starting substances, the course of process (b) according to the invention can be represented by the following equation:

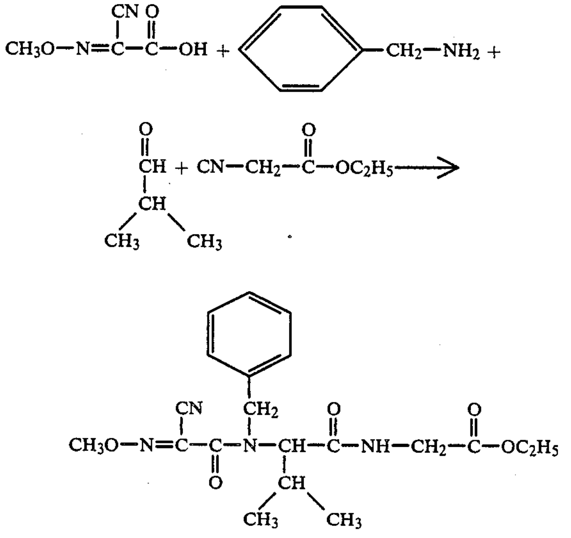

If, for example, N-(2-cyano-2-methoximinacetyl)glycine ethyl ester and methylamine are used as starting substances, the course of process (c) according to the invention can be represented by the following equation:

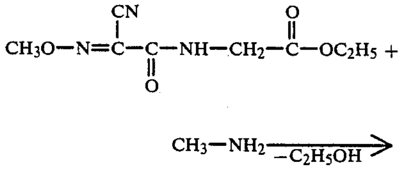

-continued

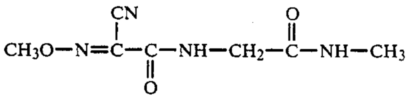

Formula (II) provides a general definition of the amino acid derivatives to be used as starting substances for carrying out process (a) according to the invention. In this formula, $R^1$, $R^2$, $R^3$ and X have the meanings which have already been mentioned for these substituents in connection with the description of the substances of the formula (I) according to the invention.

The amino acid derivatives of the formula (II) are known in some cases (compare, for example, Houben-Weyl, Methoden der organischen Chemie (Methods of Organic Chemistry), Volume, XV, part 1 and 2, Georg Thieme Verlag, Stuttgart 1974; and R. C. Sheppard, A Specialist Periodical Report, Amino acids, Peptids and Proteins, The Royal Society of Chemistry, Burlington House, London 1978, and I. P. Greenstein and M. Winitz, Chemistry of Amino Acids, I. Wiley Sons Inc., New York, London 1961; and E. Schröder and K. Lübke, The Peptides Volume I, Academic Press, New York, London 1965), or they can be obtained by the processes described therein.

Formula (III) provides a general definition of the carboxyl-activated derivatives of E-isomers of carboxylic acids also to be used as starting substances for carrying out process (a) according to the invention and likewise process (b). In this formula, R has the abovementioned meaning.

The carboxyl-activated derivatives of E-isomers of carboxylic acids of the formula (III) are not known, with the exception of the E-isomer of 2-cyano-2-methoximinoacetic acid (compare I. J. Belasco and F. J. Baude, Pestic. Sci., 12, 27, 1981). The carboxyl-activated derivatives of carboxylic acids of the formula (III) are obtained by a procedure in which, in accordance with generally known processes, the carboxylic acid esters of the formula (VIII)

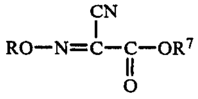
(VIII)

in which

R has the abovementioned meaning and $R^7$ represents alkyl, preferably methyl or ethyl, are first reacted with an alkali metal hydroxide, such as, for example, sodium hydroxide, and then with an acid, such as, for example, hydrochloric acid or sulphuric acid, or with an acid ion exchanger, in the presence of a diluent, such as, for example, water, alcohols, ethers or mixtures of alcohols or ethers with water, at temperatures between 0° and 80° C., preferably between 20° and 40° C.

The hydrolysis is preferably carried out with potassium hydroxide in the presence of a water/ethanol mixture, the reaction mixture being evaporated in vacuo at 20° C. and the potassium salt formed being reacted with, for example, oxalyl chloride to give the corresponding acid chloride (compare also the preparation examples).

The carboxylic acid esters of the formula (VIII) are known in some cases (compare I. J. Belasco and F. J. Baude, Pestic, Sci., 12, 27, 1981), or they can be obtained by the process described therein, by a procedure in which the E-isomers of carboxylic acid esters of the formula (IX)

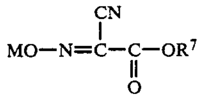
(IX)

in which
$R^7$ has the abovementioned meaning and
M represents hydrogen, sodium or potassium, preferably sodium,
are reacted with a compound of the formula (X)

R—W (X)

in which
R has the abovementioned meaning and
W represents halogen or a sulphonyldioxy or sulphonyloxy radical, such as, preferably, chlorine, bromine, iodine, $-OSO_2OCH_3$, $-OSO_2OC_2H_5$, $-OSO_2CH_3$ or

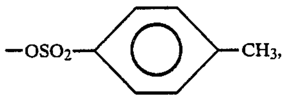

if appropriate in the presence of a base, such as, for example, potassium carbonate, triethylamine or diazabicycloundecane (DBU), and in the presence of a solvent, such as, for example, acetone, dimethylformamide, dimethylsulphoxide or acetonitrile, at temperatures between 0° and 120° C.

The E-isomers of carboxylic acid esters of the formula (IX) are known (compare, for example, G, Kinast, Liebigs Ann. Chem., 1981, 1561; M. Conrad and A. Schulze, Ber. dtsch. chem. Ges., 42, 735, 1909), and they can be obtained by the processes described therein.

The compounds of the formula (X) are generally known alkylating agents.

Possible carboxyl-activated derivatives of the carboxylic acids of the formula (III) are all the carboxylactivated derivatives, such as acid halides, such as, for example, acid chlorides, acid azides, and furthermore symmetric and mixed anhydrides, such as, for example, mixed 0-alkylcarbonic acid anhydrides, and also activated esters, such as, for example, p-nitrophenyl esters or N-hydroxysuccinimide esters, and activated forms of carboxylic acids produced in situ with condensing agents, such as, for example, dicyclohexylcarbodiimide or carbonyldiimidazole.

The acid chlorides corresponding to the carboxylic acids of the formula (III) are preferably employed. They can be prepared by a procedure in which the carboxylic acids of the formula (III), or salts thereof, are reacted with a halogenating agent, such as, for example, phosphorus pentachloride, thionyl chloride or oxalyl chloride, in the generally known manner. The use of oxalyl chloride together with the sodium or potassium salt of the carboxylic acid of the formula (III) is preferred, since isomerization is minimal under these conditions.

The acylation with the carboxyl-activated derivatives can be carried out in an aqueous or non-aqueous medium; suitable media here are ketones, such as, for example, acetone; esters, such as, for example, ethyl acetate; amides, such as, for example, dimethylformamide, nitriles, such as, for example, acetonitrile, chlorohydrocarbons, such as, for example, methylene chloride, hydrocarbons, such as, for example, toluene; or ethers, such as, for example, tetrahydrofuran, or mixtures thereof.

The acylation with an acid halide can be carried out in the presence of an acid-binding agent, such as, preferably, a tertiary amine, such as, for example, triethylamine, pyridine or an inorganic base, such as, for example, sodium carbonate or calcium carbonate.

Formula (VI) provides a general definitiOn Of the isonitriles to be used as starting substances for carrying out process (b) according to the invention. In this formula, $R^5$ preferably represents straight-chain or branched alkyl with 1 to 4 carbon atOms or represents alkenyl or alkinyl with in each case 2 to 4 carbon atoms, or represents cyanoalkyl with 1 to 4 carbon atoms in the alkyl part, or represents alkoxycarbonylalkyl with in each case 1 to 4 carbon atoms in the alkoxy part and in the alkyl part, or furthermore represents cycloalkyl which has 3 to 7 carbon atoms and is optionally mono-, di- or trisubstituted by identical or different substituents, preferred substituents which may be mentioned being halogen and alkyl with 1 to 4 carbon atoms, or represents phenylalkyl which has 1 to 4 carbon atoms in the alkyl part and is optionally mono-, di- or trisubstituted in the phenyl part by identical or different substituents, or represents phenyl which is mono-, di- or trisubstituted by identical or different substituents, preferred possible substituents in each case being the phenylalkyl substituents already mentioned as preferred for R.

The isonitriles of the formula (VI) are known in some cases (compare, for example, I. Ugi, Isonitrile Chemistry, Academic Press, New York, 1971), or they can be prepared in an analogous manner by generally known processes, by reacting the corresponding formylated primary amines with, for example, phosgene or phosphorus oxychloride in the presence of a tertiary amine, such as, for example, pyridine or triethylamine, water being split off.

Formula (IV) or (V) provides a general definition of the amines and carbonyl derivatives also to be used as starting substances for carrying out process (b) according to the invention. In these formulae, $R^1$ or $R^2$ and $R^3$ have the abovementioned meanings.

The amines of the formula (IV) and the carbonyl derivatives of the formula (V) are generally known compounds of organic chemistry.

Formula (Ia) provides a general definition of the amino acid derivatives which are to be used as starting substances for carrying out process (c) according to the invention and which are part of the invention. In this formula, R, $R^2$ and $R^3$ preferably have the meaning which have already been mentioned for these substituents in connection with the description of the substances of the formula (I) according to the invention.

Possible acylating agents corresponding to the amino acid derivatives of the formula (Ia) are all the carboxyl-activated derivatives which have already been mentioned in connection with the acylating agent corresponding to the carboxylic acid derivatives of the formula (III), preferably azides, 0-alkylcarbonic acid anhydrides and activated derivatives produced in situ with dicyclohexylcarbodiimide.

The amino acid derivatives of the formula (Ia) are compounds according to the invention and can be prepared by process (a) according to the invention.

Formula (VII) provides a general definition of the amines also to be used as starting substances for carrying out process (c) according to the invention. In this formula, $R^{II}$ and $R^{III}$ have the abovementioned meanings.

The amines of the formula (VII) are generally known compounds of organic chemistry.

Formula (Ib) provides a general definition of the amino acid derivatives to be used as starting substances for carrying out process (d) according to the invention. In this formula, R, $R^2$ and $R^3$ preferably have the meanings which have already been mentioned for these substituents in connection with the description of the substances of the formula (I) according to the invention. $R^6$ preferably represents methyl or ethyl.

The amino acid derivatives of the formula (Ib) are compounds according to the invention.

Possible diluents for process (a) according to the invention are water and inert organic solvents. These include ketones, such as acetone or ethyl methyl ketone; esters, such as ethyl acetate or methyl acetate; amides, such as dimethylformamide; nitriles, such as acetonitrile; chlorohydrocarbons, such as methylene chloride or carbon tetrachloride; hydrocarbons, such as toluene or ethers, such as tetrahydrofuran; or mixtures thereof.

Possible acid-binding agents for process (a) according to the invention are the customary inorganic and organic acid-binding agents. These include, preferably, tertiary amines, such as triethylamine, pyridine or N-methylmorpholine; as well as inorganic bases, such as sodium carbonate or calcium carbonate.

If appropriate, process (a) according to the invention is carried out in the presence of a catalyst. Examples which may be mentioned are 4-dimethylaminopyridine, 1-hydroxy-benzotriazole or dimethylformamide.

The temperatures can be varied within a substantial range in carrying out process (a). The process is in general carried out between −60° and +120° C., preferably at −20° to +40° C.

In carrying out process (a) according to the invention, equimolar amounts are preferably used.

The amino acid derivatives of the formula (II) are employed here as pure optical isomers (D or L form) or as racemates.

Possible diluents for process (b) according to the invention are all the customary inert organic solvents. These include, preferably, alcohols, such as methanol or ethanol; ethers, such as diethyl ether, chlorinated hydrocarbons, such as chloroform or carbon tetrachloride; and ketones, such as acetone.

The temperatures can be varied within a substantial range in carrying out process (b) according to the invention. The process is in general carried out between −20° and +40° C., preferably at 0° to 20° C.

In carrying out process (b) according to the invention, equimolar amounts are preferably used.

Possible diluents, catalysts and acid-binding agents for process (c) according to the invention correspond to those of process (a).

The temperatures can be varied within a substantial range in carrying out process (c) according to the invention. The process is in general carried out between −60° and +120° C., preferably at −20° to +40° C.

In carrying out process (c) according to the invention, equimolar amounts are preferably used.

Possible diluents for process (d) according to the invention are, preferably, alcohols, such as, for example, methanol, ethanol or isopropanol.

The temperatures can be varied within a substantial range in carrying out process (d) according to the invention. The process is in general carried out between −20° and +60° C., preferably at 0° to 20° C.

In carrying out process (d) according to the invention, 1 to 10 moles of amine of the formula (VII) are preferably employed per mole of the compounds of the formula (Ib).

The metal salt complexes of compounds of the general formula (I) can be obtained in a simple manner by customary processes, thus, for example, by dissolving the metal salt in alcohol, for example ethanol, and adding the solution to the compounds of the general formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as pest combating agents.

Fungicidal agents in plant protection are employed, for example, for combating Plasmodiophoromycetes, Oomycetes, Chytridiomycetes, Zygomycetes, Ascomycetes, Basidiomycetes and Deuteromycetes.

Some pathogens of fungal diseases which fall under the generic names listed above may be mentioned as examples but not by way of limitation.

Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As agents for combating pests, the active compounds according to the invention can be employed with particularly good success for combating Plasmopara species, such as, for example, *Plasmopora viticola,* on vines, and Phytophthora species, such as, for example, *Phytophthora infestans,* on tomatoes. It should be particularly emphasized that the active compounds according to the invention not only display a protective action but in some cases also have a curative action, that is to say when used after contamination with spores of the fungus. The partly systemic action of the substances should also be pointed out. Thus, it is possible to protect plants from fungal attack if the active compound is fed to the above-ground parts of the plant via the soil and the root or via the seed.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gasses under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellents, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example nonionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

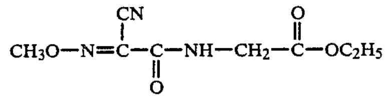

Process a 60.5 g (0.427 mole) of glycine ethyl ester hydrochloride are suspended in 450 ml of methylene chloride, 86.2 g (0.853 mole) of triethylamine and 5.2 g (0.043 mole) of 4-dimethylaminopyridine are added, the reaction mixture is stirred at 20° C. for 15 minutes and a solution of 62.5 g (0.427 mole) of 2-cyano-2-methoximino-acetyl chloride (E-isomer) is added dropwise at 0° C. in the course of one hour. The reaction mixture is then stirred at 0° C. for one hour and then at room temperature for 5 hours and the solution is left to stand at room temperature for 2 days. After washing with 1M hydrochloric acid (2 portions of 300 ml each), saturated sodium bicarbonate solution (2 portions of 200 ml each) and water (2 portions of 300 ml each), the solution is dried over sodium sulphate and evaporated in vacuo.

81.0 g (89% of theory) of $N^{\alpha}$-(2-cyano-2-methoximino-acetyl)-glycine ethyl ester (E-isomer) are obtained as a brown oil of refractive index $n_D^{23}$ 1.4699.

Preparation of the Starting Substance

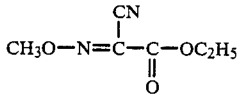
(a)

161 g (1.25 moles) of dimethyl sulphate (98% pure) are added dropwise to a suspension of 164 g (1 mole) of ethyl 2-cyano-2-hydroximinoacetate, sodium chloride (G. Kinast, Libiegs Ann. Chem., 1981, 1561) and 138 g of powdered potassium carbonate in 1.5 l of acetone in the course of 30 minutes and the reaction mixture is heated under reflux for 3 hours. After cooling, it is filtered over kieselguhr and evaporated.

124.8 g of ethyl 2-cyano-2-methoximino-acetate (E-isomer) are obtained as an 85% pure (gas chromatogram) red-brown oil. The yield is accordingly 68% of theory. After chromatography on five times the amount of silica gel 60 with chloroform, a 93% pure pale yellow oil is obtained.

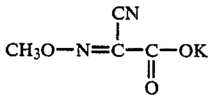
(b)

A solution of 45.1 g (0.806 mole) of potassium hydroxide in 500 ml of water is added dropwise to a solution of 124.8 g (0.672 mole) of 84% pure ethyl 2-cyano-2-methoximino-acetate (E-isomer) in 500 ml of ethanol at 20° C. and the reaction mixture is stirred at 40° C. for one hour. The solution is evaporated in vacuo at 40° C. and the residue is stirred with methanol for 30 minutes, filtered off with suction, washed with ethanol, acetonitrile and methylene chloride and dried at room temperature.

58.6 g (53% of theory) of the potassium salt of 2-cyano-2-methoximino-acetate (E-isomer) are obtained.

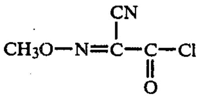
(c)

20 g (0.12 mole) of the potassium salt of 2-cyano-2-methoximino-acetate (E-isomer) are Suspended in 250 ml of dry ether and, after addition of a few drops of dimethylformamide, 76.2 g (0.6 mole) of oxalyl chloride are added dropwise at 0° C. The reaction mixture is stirred at 0° C. for 2 hours and filtered and the filtrate is evaporated in vacuo at room temperature.

13.5 g (77% of theory) of 2-cyano-2-methoximinoacetyl chloride (E-isomer) are obtained as a yellow oil, which is further reacted immediately.

EXAMPLE 2

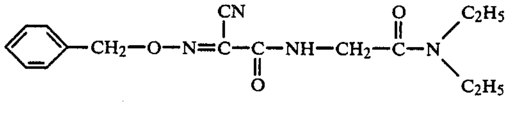

Process a

A solution of 11.1 g (0.05 mole) of 2-benzyloximino-2-cyano-acetyl chloride (E-isomer) in 50 ml of methylene chloride is added dropwise to a solution of 5.8 g (0.02 mole) of glycine diethylamide, 5.05 g (0.05 mole) of triethylamine and 0.61 g (0.005 mole) of 4-dimethylaminopyridine in 75 ml of methylene chloride at 0° C., and the reaction mixture is stirred at 0° C. for one hour and at room temperature for 20 hours. The reaction mixture is diluted with 50 ml of methylene chloride, washed with 1M hydrochloric acid, 10% strength sodium bicarbonate solution and water, dried over magnesium sulphate and evaporated in vacuo. The residue is recrystallized from ligroin/ethyl acetate.

4.0 g (25% of theory) of $N^{\alpha}$-(2-benzyloximino-2-cyano-acetyl)-glycine diethylamid (E-isomer) of melting point 76°-81° C. are obtained.

EXAMPLE 3

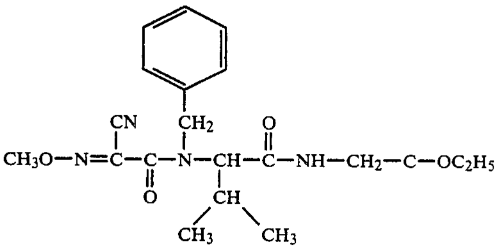

Process b

A solution of 13.6 g (0.12 mole) of ethyl isocyanoacetate (D. Hoppe and U. Schollkopf, Liebigs Ann. Chem., 763, 1, 1972) in 100 ml of methanol is added dropwise to a solution of 15.3 g (0.12 mole) of 2-cyano-2-methoximinoacetic acid (E-isomer), 8.65 g (0.12 mole) of isobutyraldehyde and 12.85 g (0.12 mole) of benzylamine in 150 ml of methanol at 0° C. The reaction mixture is allowed to come to room temperature and is stirred at 20° C. for 13 hours. The solvent is distilled off in vacuo, the residue is partitioned between 300 ml each of water and ethyl acetate and the organic phase is washed with 200 ml each of 1M hydrochloric acid, 10% strength sodium bicarbonate solution and water, dried over sodium sulphate and evaporated in vacuo. 14.4 g (30% of theory) of N-[α-benzyl-$N^{\alpha}$-(2-cyano-2-methoximino-acetyl)-DL-valyl]-glycine ethyl ester (E-isomer) are obtained as a brown oil.

Preparation of the Starting Substance

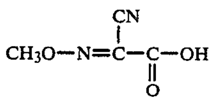

550 ml (0.55 mole) of 1M sodium hydroxide solution are added dropwise to a mixture of 83 g (0.5 mole) of ethyl 2-cyano-2-methoximino-acetate (E-isomer) and 250 ml of water at 20°-30° C. and the reaction mixture is stirred at room temperature for 3½ hours. The solution is washed with ether and discharged onto a column of 1 l of Lewatit S 100 (H+ form, washed beforehand with acetone). The column is eluted with in each case 1 l of acetone and acetonitrile and the eluate is evaporated in vacuo at 30°-40° C. 63.2 g (99% of theory) of 2-cyano-2-methoximinoacetic acid (E-isomer) of melting point 48°-49° C. are obtained.

EXAMPLE 4

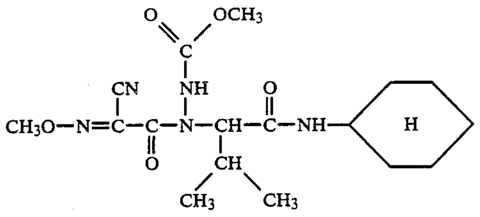

Process b

A solution of 5.5 g (0.05 mole) of cyclohexyl isocyanide is added dropwise to a solution of 6.4 g (0.05 mole) of 2-cyano-2-methoximino-acetic acid (E-isomer), 4.5 g (0.05 mole) of methyl carbazate and 3.6 g (0.05 mole) of isobutyraldehyde in 75 ml of methanol at 0° C. and the mixture is stirred at room temperature for 24 hours. The solvent is distilled off in vacuo, the residue is partitioned between in each case 200 ml of ethyl acetate and water and the organic phase is washed with in each case 150 ml of 1M hydrochloric acid, 10% strength sodium bicarbonate solution and water, dried over sodium sulphate and concentrated in vacuo.

9.0 g (47% of theory) of N$^{\alpha}$-(2-(cyano-2-methoximinoacetyl)-N$^{\alpha}$-methoxycarbonylamino-DL-valine cyclohexylamide (E-isomer) of melting point 132°-134° C. are obtained.

EXAMPLE 5

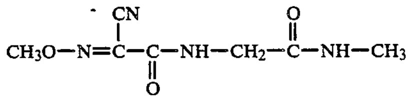

Process c 24.5 ml (0.166 mole) of a 6.8M solution of methylamine in methanol are added dropwise to a solution of 11.8 g (0.0553 mole) of N-(2-cyano-2-methoximino-acetyl)glycine ethyl ester (E-isomer) in 50 ml of methanol at 0° C. The reaction mixture is allowed to come to room temperature and is stirred at 20° C. for a further hour. After cooling to 10° C., the crystalline precipitate is filtered off with suction, washed with a little cold ethanol and dried at 40° C.

7.0 g (64% of theory) of N$^{\alpha}$-(2-cyano-2-methoximinoacetyl)-glycine methylamide (E-isomer) of melting point 140°-141° C. are obtained.

EXAMPLE 6

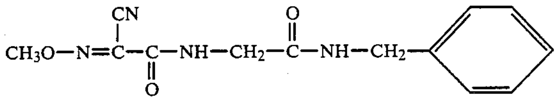

Process c

A solution of 7.0 g (0.0712 mole) of concentrated hydrochloric acid in 10 ml of tetrahydrofuran is added to a solution of 7.1 g (0.0356 mole) of N$^{\alpha}$-(2-cyano-2-methoximino-acetyl)-glycine hydrazide (E-isomer) in 70 ml of dimethylformamide, and 5.15 g (0.042 mole) of isoamyl nitrile (97% pure) are added dropwise at −20° C. After the mixture has been stirred at −20° C. for 15 minutes, a solution of 10.8 g (0.107 mole) of triethylamine in 15 ml of dimethylformamide is added dropwise at −20° C. and a solution of 4.2 g (0.0392 mole) of benzylamine in 3.5 ml of dimethylformamide is then added. The reaction mixture is kept at 0° C. for 65 hours, stirred at 20° C. for 24 hours and then poured into 150 ml of water. The mixture is extracted with ethyl acetate (2 portions of 150 ml each) and the extract is washed with in each case 100 ml of 1M citric acid, 10% strength sodium bicarbonate solution and water, dried over sodium sulphate and concentrated in vacuo.

6.2 g (64% of theory) of N$^{\alpha}$-(2-cyano-2-methoximinoacetyl)-glycine benzylamide (E-isomer) of melting point 101°-102° C. are obtained.

Preparation of the Starting Substances

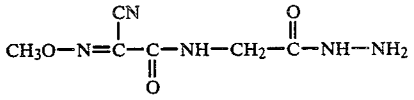

15.5 g (0.31 mole) of hydrazine hydrate are added dropwise to a solution of 30 g (0.155 mole) of N-(2-cyano-2-methoximino-acetyl)-glycine ethyl ester (E-isomer) in 150 ml of ethanol at 24°-30° C. and the reaction mixture is stirred at room temperature for 4 hours. After cooling to 10° C., the crystalline precipitate is filtered off with suction, washed with 200 ml of ether and dried at room temperature.

28.1 g (91% of theory) of N$^{\alpha}$-(2-cyano-2-methoximino-acetyl)-glycine hydrazide (E-isomer) of melting point 167°-168° C. are obtained.

The following E-isomers of the compounds of the general formula (I)

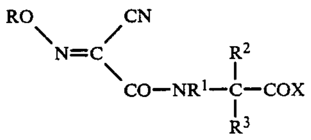

(I)

are obtained in an analogous manner and in accordance with the processes according to the invention:

| Example No. | R | $R^1$ | $R^2$ | $R^3$ | X | Physical constants |
|---|---|---|---|---|---|---|
| 7 | $-CH_3$ | 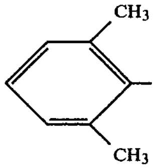 | H | $-CH_3$ | $-OCH_3$ | Melting point: 85–87° C. |
| 8 | $-CH_3$ | 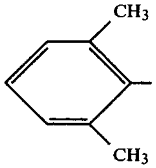 | H | $-C_2H_5$ | $-OCH_3$ | Oil |
| 9 | $-CH_3$ | H | H | 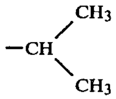 | 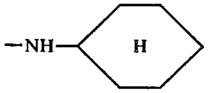 | Melting point: 144–146° C. |
| 10 | $-CH_3$ | 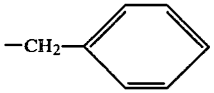 | H | H | 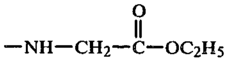 | $n_D^{20}$: 1.5122 |
| 11 | $-CH_3$ | H | H | H | 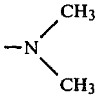 | Melting point: 102–104° C. |
| 12 | 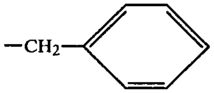 | H | H | 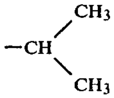 | $-OCH_3$ | Melting point: 46–52° C. |
| 13 | 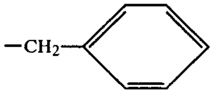 | H | H | 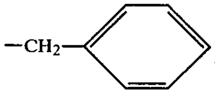 | $-OCH_3$ | Melting point: 67–71° C. |

-continued
| Example No. | R | R1 | R2 | R3 | X | Physical constants |
|---|---|---|---|---|---|---|
| 14 | 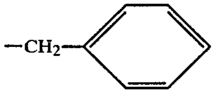 | H | H | $-CH_2OH$ | $-OCH_3$ | Melting point: 73-74° C. (L-form) |
| 15 | 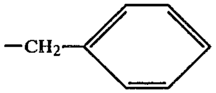 | $-CH_3$ | H | H | 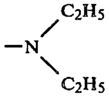 | $n_D^{20}$: 1.5190 |
| 16 | 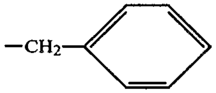 | H | $-C_2H_5$ | $-C_2H_5$ | $-NH_2$ | Melting point: 70-74° C. |
| 17 | 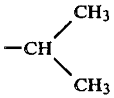 | H | H | H | $-OC_2H_5$ | Melting point: 74-76° C. |
| 18 | 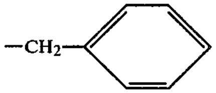 | H | H | H | $-OC_2H_5$ | $n_D^{20}$: 1.5175 |
| 19 | 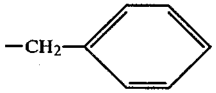 | H | H | 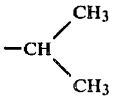 | $-OCH_3$ | Melting point: 67-71° C. |
| 20 | 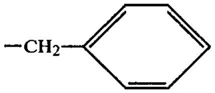 | H | H | 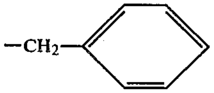 | $-NH-CH_3$ | Oil (L-Form) |
| 21 | 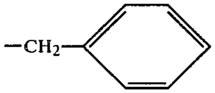 | H | H | $-CH_2OH$ | $-OCH_3$ | $n_D^{20}$: 1,5223 |

-continued
| Example No. | R | R¹ | R² | R³ | X | Physical constants |
|---|---|---|---|---|---|---|
| 22 | 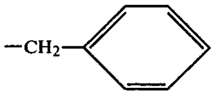 | H | H | 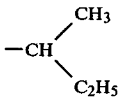 | $-OCH_3$ | Melting point: 71-74° C. |
| 23 | 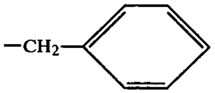 | H | H | $-CH_3$ | $-OCH_3$ | Melting point: 60-62° C. |
| 24 | 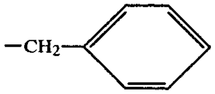 | H | H | $-CH_3$ | $-OCH_3$ | Melting point: 59-62° C. (L-Form) |
| 25 | 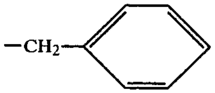 | H | H | 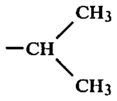 | $-NH-CH_3$ | Oil |
| 26 | 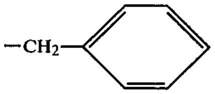 | H | H | H | $-NH-CH_3$ | Melting point: 122-125° C. |
| 27 | 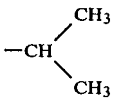 | H | H | H | $-NH-CH_3$ | Melting point: 102-104° C. |
| 28 | 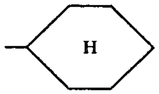 | H | H | H | $-OC_2H_5$ | Melting point: 47-50° C. |
| 29 | 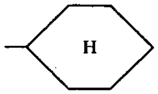 | H | H | H | $-NH-CH_3$ | Melting point: 136-140° C. |

-continued
| Example No. | R | R[1] | R[2] | R[3] | X | Physical constants |
|---|---|---|---|---|---|---|
| 30 | 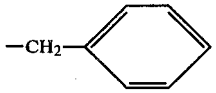 | H | H | $-CH_3$ | $-NH-CH_3$ | Melting point: 177-181° C. |
| 31 | 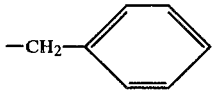 | H | H | H | 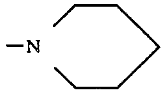 | Melting point: 119-120° C. |
| 32 | 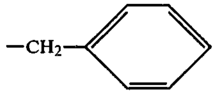 | H | H | 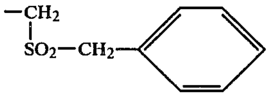 | $-OC_2H_5$ | Melting point: 105-107° C. (L-Form) |
| 33 | 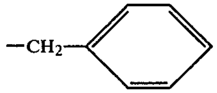 | H | H | H | 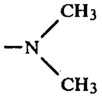 | Melting point: 132-138° C. |
| 34 | 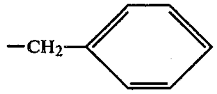 | H | H | H | 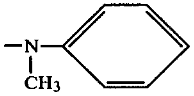 | Melting point: 85-89° C. |
| 35 | 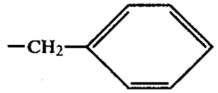 | H | H | H | 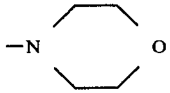 | Melting point: 127-128° C. |
| 36 | 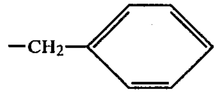 | H | H | H | 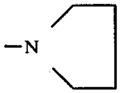 | Melting point: 97-101° C. |
| 37 | $-CH_3$ | H | H | H | 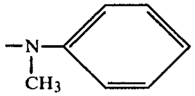 | Melting point: 154-155° C. |

-continued

| Example No. | R | $R^1$ | $R^2$ | $R^3$ | X | Physical constants |
|---|---|---|---|---|---|---|
| 38 | $-CH_3$ | H | H | H | 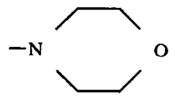 | Melting point: 172-173° C. |
| 39 | $-CH_3$ | H | H | H | 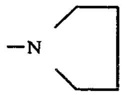 | Melting point: 101-105° C. |
| 40 | $-CH_3$ | H | H | H | 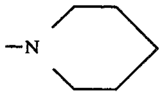 | Melting point: 137-139° C. |
| 41 | $-CH_3$ | H | H | H | $-OH$ | Melting point: 95-100° C. |
| 42 | $-CH_3$ | H | H | H | $-NH-C_2H_5$ | Melting point: 108-110° C. |
| 43 | $-CH_3$ | H | H | $-CH_3$ | $-NH_2$ | Melting point: 129-130° C. (L-Form) |
| 44 | $-CH_3$ | H | H | 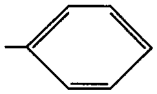 | $-OCH_3$ | Melting point: 98-99° C. (D-Form) |
| 45 | $-CH_3$ | H | H | H | $-N(C_2H_5)_2$ | Melting point: 93-94° C. |
| 46 | $-CH_3$ | H | H | $-CH_2-CH(CH_3)_2$ | $-NH_2$ | Oil (L-Form) |
| 47 | $-CH_3$ | H | $-CH_3$ | $-CH_3$ | $-OCH_3$ | $n_D^{20}$: 1.4683 |
| 48 | $-CH_3$ | H | $-C_2H_5$ | $-C_2H_5$ | $-NH_2$ | Melting point: 218-220° C. |
| 49 | $-CH_3$ | H | H | H | $-NH_2$ | Melting point: 136-138° C. |
| 50 | $-CH_3$ | $-CH_3$ | H | H | $-OCH_3$ | $n_D^{23}$: 1.4720 |
| 51 | $-CH_3$ | $-CH_3$ | H | $-CH_3$ | $-OCH_3$ | $n_D^{22}$: 1.4705 |
| 52 | $-CH_3$ | $-CH_3$ | H | H | $-N(C_2H_5)_2$ | $n_D^{23}$: 1.4857 |
| 53 | $-CH_3$ | 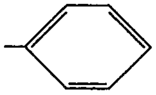 | H | H | $-OCH_3$ | $n_D^{23}$: 1.5268 |

-continued
| Example No. | R | $R^1$ | $R^2$ | $R^3$ | X | Physical constants |
|---|---|---|---|---|---|---|
| 54 | 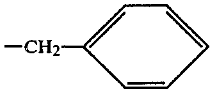 | $-CH_3$ | H | H | $-OCH_3$ | $n_D^{20}$: 1.5202 |
| 55 | 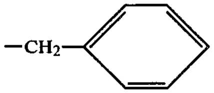 | H | $-CH_3$ | $-CH_3$ | $-OCH_3$ | Melting point: 40-45° C. |
| 56 | $-CH_3$ | H | H | H | 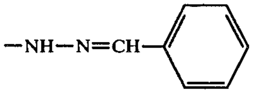 | Melting point: 204-206° C. |
| 57 | 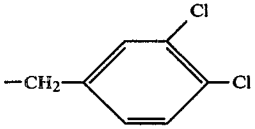 | H | H | H | $-OC_2H_5$ | $n_D^{23}$: 1.5346 |
| 58 | 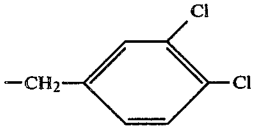 | H | H | H | $-NHCH_3$ | Melting point: 165-168° C. |
| 59 | 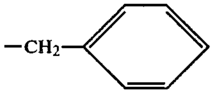 | H | H | $-CH(CH_3)_2$ | $-NHCH_3$ | Oil |
| 60 | 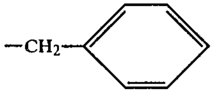 | H | H | $-CH_3$ | $-NHCH_3$ | Oil |
| 61 | $-CH_3$ | H | H | 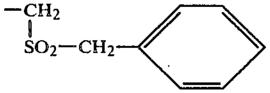 | $-OC_2H_5$ | Melting point: 74-76° C. |
| 62 | $-CH_3$ | H | H | H | $-OC_2H_5$ | Melting point: 69-71° C. |

-continued

| Example No. | R | $R^1$ | $R^2$ | $R^3$ | X | Physical constants |
|---|---|---|---|---|---|---|
| 63 | $-CH_3$ | $-CH_3$ | H | $-CH_3$ | $-OH$ | Oil |
| 64 | 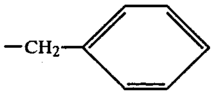 | 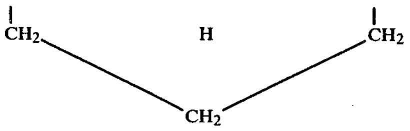 | H | | $-OCH_3$ | $n_D^{20}$: 1.5305 (L-Form) |
| 65 | $-CH_3$ | H | H | H | $-NH-CH_2-CH=CH_2$ | Melting point: 85-88° C. |
| 66 | $-CH_2-CH=CH_2$ | H | H | H | $-OC_2H_5$ | Oil |
| 67 | $-CH_2-C\equiv CH$ | H | H | H | $-OC_2H_5$ | Oil |
| 68 | $-CH_3$ | H | $-CH_3$ | H | $-NH-CH_3$ | Melting point: 118° C. |
| 69 | $-C_2H_5$ | H | H | H | $-NH-CH_3$ | Melting point: 144° C. |
| 70 | $-CH_2-CH=CH_2$ | H | H | H | $-NH-CH_3$ | Melting point: 133° C. |
| 71 | $-CH_2-C\equiv CH$ | H | H | H | $-NH-CH_3$ | Melting point: 148-150° C. |
| 72 | $-CH_3$ | H | H | H | $-NH-CH_2-CO-OC_2H_5$ | Melting point: 123-125° C. |
| 73 | $-CH_3$ | H | H | $-CH(CH_3)_2$ | $-NH-CH_3$ | Melting point: 130° C. |
| 74 | $-CH_3$ | H | H | 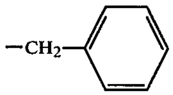 | $-NH-CH_3$ | Melting point: 50° C. |
| 75 | $-CH_3$ | H | H | $-CH(CH_3)_2$ | $-NH-CH_3$ | Melting point: 130° C. |
| 76 | 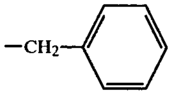 | H | H | $-CH_3$ | $-NH-NH-CO-NH-CH_3$ | Melting point: 178° C. (L-form) |
| 77 | 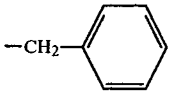 | H | H | $-CH_3$ | $-NH-NH-CO-NH-CH_3$ | Melting point: 135° C. (DL-form) |
| 78 | 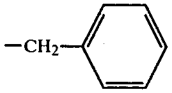 | H | H | $-CH_2-OH$ | $-NH-NH-CO-NH-CH_3$ | Melting point: 219° C. |
| 79 | $-CH_3$ | H | H | $-C(CH_3)_3$ | $-NH_2$ | Melting point: 219-223° C. |

-continued

| Example No. | R | $R^1$ | $R^2$ | $R^3$ | X | Physical constants |
|---|---|---|---|---|---|---|
| 80 | $-CH_3$ | H | H | 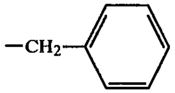 | $-NH-CH_3$ | Melting point: 198-200° C. |
| 81 | $-CH_3$ | H | H | 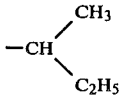 | $-NH-CH_3$ | Melting point: 118-120° C. |
| 82 | $-CH_3$ | H | H | H | $-NH-CH_2-CO-NH-CH_3$ | Melting point: 212-214° C. |
| 83 | 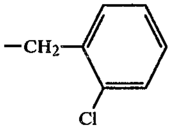 | $-CH_3$ | H | H | $-OCH_3$ | Oil |
| 84 | $-CH_3$ | H | H | $-CH_2-CH(CH_3)_2$ | $-NH-CH_3$ | Oil |
| 85 | $-CH_3$ | H | H | 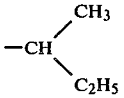 | $-NH-CH_3$ | Melting point: 125-126° C. |
| 86 | $-CH_3$ | H | 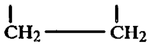 | | $-NH-CH_3$ | Melting point: 98-100° C. |
| 87 | $-CH_3$ | H | H | 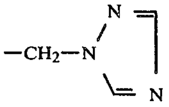 | $-NH-CH_3$ | Melting point: 151-152° C. |
| 88 | $-CH_3$ | H | H | $-CH_3$ | $-NH-CH_3$ | Melting point: 157-158° C. |
| 89 | $-CH_3$ | 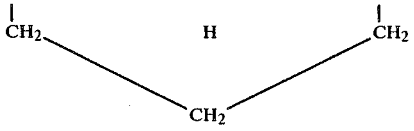 | H | | $-NH-CH_3$ | Melting point: 148-149° C. |

-continued

| Example No. | R | $R^1$ | $R^2$ | $R^3$ | X | Physical constants |
|---|---|---|---|---|---|---|
| 90 | $-CH_3$ | H | H | 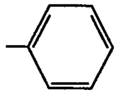 | $-NH-CH_3$ | Oil |
| 91 | $-CH_3$ | H | H | 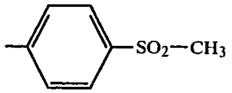 | $-NH-CH_3$ | Melting point: 211-212° C. |
| 92 | $-CH_3$ | H | H | H | $-NH-C(CH_3)_3$ | Melting point: 152-153° C. |
| 93 | $-CH_3$ | H | H | H | $-NH-CH_2-CH_2-N(C_2H_5)_2$ | Oil |
| 94 | $-CH_3$ | H | H | H | $-NH-CH(CH_3)_2$ | Melting point: 132-133° C. |
| 95 | $-CH_3$ | H | H | H | 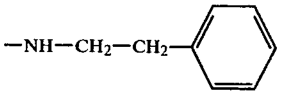 | Melting point: 92-95° C. |
| 96 | $-CH_3$ | H | H | H | 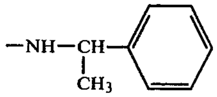 | Melting point: 96-98° C. |
| 97 | $-CH_3$ | H | H | H | $-NH-CH_2-CH_2-Cl$ | Melting point: 91-94° C. |
| 98 | $-CH_3$ | H | H | H | $-NH-CH(CH_3)_2$ | Melting point: 86-88° C. |
| 99 | $-CH_3$ | H | H | H | $-NH-C(CH_3)_3$ | Melting point: 80-81° C. |
| 100 | $-CH_3$ | H | H | H | $-NH-CH_2-CH(CH_3)_2$ | Melting point: 100-102° C. |
| 101 | $-CH_3$ | H | H | H | $-NH-CH(CH_3)-CH_2-CH_3$ | Melting point: 111-112° C. |
| 102 | $-CH_3$ | H | H | H | $-NH-CH_2-CH_2-O-CH_3$ | Melting point: 102-105° C. |
| 103 | $-CH_3$ | H | H | H | $-NH-CH_3 \times \frac{1}{2}CuCl_2$ | Melting point: 160-165° C. |
| 104 | $NC-CH_2-$ | H | H | H | $-NH-CH_3$ | Melting point: 135-38° C. |

-continued

| Example No. | R | $R^1$ | $R^2$ | $R^3$ | X | Physical constants |
|---|---|---|---|---|---|---|
| 105 | $CH_3$ | H | H | H | 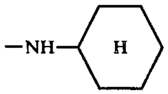 | Melting point: 135-36° C. |
| 106 | $CH_3$ | H | H | H | 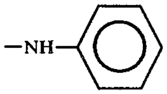 | Melting point: 175-78° C. |
| 107 | $CH_3$ | H | H | H | 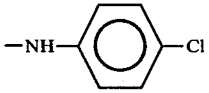 | Melting point: 195-98° C. |
| 108 | $CH_3$ | H | H | H | 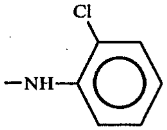 | Melting point: 111-12° C. |
| 109 | $CH_3$ | H | H | H | 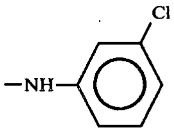 | Melting point: 215-16° C. |
| 110 | $CH_3$ | H | H | H | 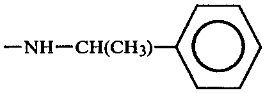 | Melting point: 104-06° C. |
| 111 | $CH_3$ | H | H | H | 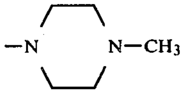 | Melting point: 160-61° C. |
| 112 | $CH_3$ | H | H | H | $-N(CH_3)-CH_2-COOCH_3$ | Melting point: 82-83° C. |
| 113 | $CH_3$ | H | H | H | $-NH-CH_2CH_2-COOCH_3$ | Melting point: 73-74° C. |
| 114 | $CH_3$ | H | H | H | $-NH-CH(CH_3)-COOCH_3$ (pure optical isomer) | Melting point: 139-40° C. |
| 115 | $CH_3$ | H | H | H | $-NH-CH(CH_3)-COOCH_3$ | Melting point: 129-30° C. |
| 116 | $CH_3$ | H | H | H | $-NH-CH_2CH_2-COOH$ | Melting point: |

-continued

| Example No. | R | $R^1$ | $R^2$ | $R^3$ | X | Physical constants |
|---|---|---|---|---|---|---|
| | | | | | | 187-85° C. |
| 117 | $CH_3$ | H | H | H | $-NH-CH(CH_3)-COOH$ (pure optical isomer) | Melting point: 146-47° C. |
| 118 | $CH_3$ | H | H | H | $-NH-CH(CH_3)-COOH$ | Melting point: 145-46° C. |
| 119 | $CH_3$ | H | H | H | $-NH-CH(CH_3)-CO-NHCH_3$ (pure optical isomer) | Melting point: 216-18° C. |
| 120 | $NC-CH_2-$ | H | H | H | $-NH-CH_2-CO-N(C_2H_5)_2$ | Melting point: 108-10° C. |
| 121 | $CH_3$ | H | H | $-CH_2-OH$ | $-NHCH_3$ | Melting point: 135-37° C. |
| 122 | $CH_3$ | H | H | $-CH_2OH$ | $-NHCH_3$ (pure optical isomer) | Melting point: 145-47° C. |
| 123 | $CH_3$ | H | H | $-CH(OH)CH_3$ | $-NHCH_3$ (pure optical isomer) | Melting point: 62-63° C. |
| 124 | $CH_3$ | H | H | $-CH(OH)CH_3$ | $-NHCH_3$ | Melting point: 117-21° C. |
| 125 | $CH_3$ | H | H | 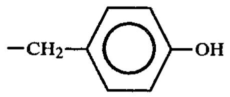 | $-NHCH_3$ (pure optical isomer) | Melting point: 152-54° C. |
| 126 | $CH_3$ | H | H | H | $-COO$ Bu-t. | Oil |
| 127 | $CH_3$ | H | H | 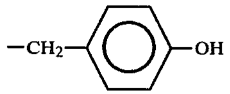 | $-NHCH_3$ | Melting point: 153-56° C. |
| 128 | $CH_3$ | H | H | $CH_3$ | $-COOH$ | Oil |
| 129 | $CH_3$ | H | H | H | $-COOH$ | Melting point: 177-78° C. (dicyclohexylamine salt) |
| 130 | $CH_3$ | H | H | $CH_3$ | $-COOH$ (pure optical isomer) | Melting point: 167-70° C. (dicyclohexylamine salt) |
| 131 | $CH_3$ | H | H | H | $-NH-CH_2-C\equiv CH$ | Melting point: 138-39° C. |
| 132 | $CH_3$ | H | H | H | $-NH-CH_2CN$ | Melting point: 154-56° C. |
| 133 | $CH_3$ | H | H | H | $-NH-CH_2CH_2CN$ | Melting point: 110-12° C. |
| 134 | $CH_3$ | H | H | H | 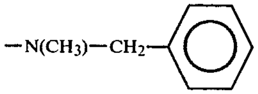 | Melting point: 90-91° C. |

-continued

| Example No. | R | $R^1$ | $R^2$ | $R^3$ | X | Physical constants |
|---|---|---|---|---|---|---|
| 135 | $CH_3$ | H | H | H | $-N(CH_3)-CH(CH_3)-C_2H_5$ | Oil |
| 136 | $CH_3$ | H | H | H | $-N(CH_3)-CH_2CH_2CN$ | Melting point: 126-27° C. |
| 137 | $CH_3$ | H | H | H | $-NH-CH(CH_3)-CONH_2$ (pure optical isomer) | Melting point: 148-50° C. |
| 138 | $CH_3$ | H | H | H | $-NH-CH(CH_3)-CONHCH_3$ | Melting point: 171-73° C. |
| 139 | $CH_3$ | H | H | H | $-NH-CH_2-CONH_2$ | Melting point: 184-86° C. |
| 140 | $CH_3$ | H | H | H | 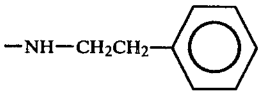 | Melting point: 115-16° C. |
| 141 | $CH_3$ | H | H | $CH_3$ | 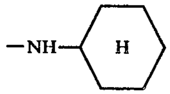 (pure optical isomer) | Melting point: 138-39° C. |
| 142 | $CH_3$ | H | H | H | 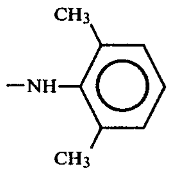 | Melting point: 211-12° C. |
| 143 | $CH_3$ | H | H | H | 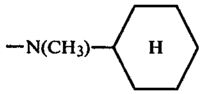 | Melting point: 95-97° C. |
| 144 | $CH_3$ | H | H | H | 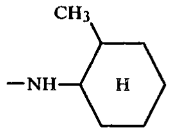 | Melting point: 128-25° C. |
| 145 | $CH_3$ | H | H | H | 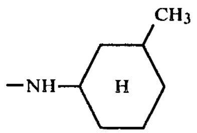 | Melting point: 119-21° C. |

-continued
| Example No. | R | $R^1$ | $R^2$ | $R^3$ | X | Physical constants |
|---|---|---|---|---|---|---|
| 146 | $CH_3$ | H | H | H | 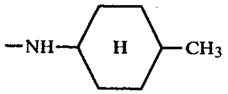 | Melting point: 99-101° C. |
| 147 | $CH_3$ | H | H | $CH_3$ | 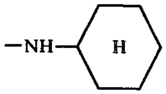 | Melting point: 138-39° C. |
| 148 | $CH_3$ | H | H | $-CH_2-CH_2-S-CH_3$ | $-NH-CH_3$ | Oil |

USE EXAMPLES

The substances shown below are employed as comparison compounds in the use examples which follow:

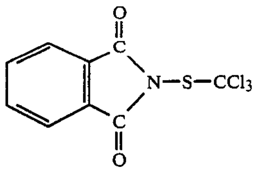

(A)

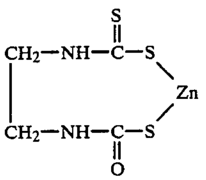

(B)

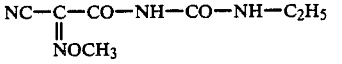

(C)

(U.S. Pat. No. 3,957,847)

EXAMPLE A

Plasmopara test (vines)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Plasmopara viticola and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, a clearly superior activity compared with the prior art is shown, for example, by the compound according to preparation Example 5.

EXAMPLE B

Phytophthora Test (tomato)/curative.
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of *Phytophthora infestans.* The plants remain in an incubation cabinet at 20° C. and 100% relative atmospheric humidity for 7 hours. After a short drying off time, the plants are sprayed with the preparation of active compound until dripping wet.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to preparation Examples 1 and 5.

EXAMPLE C

Phytophthora test (tomato)/systemic
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for systemic properties, standard soil in which young plants ready for testing have been grown is watered with the preparation of active compound. 3 days after the treatment, the plants are inoculated with an aqueous spore suspension of *Phytophthora infestans.*

The plants are placed in an incubation cabinet at 100% relative atmospheric humidity and about 20° C.

Evaluation is carried out 3 days after the inoculation.

In this test, a clearly superior activity compared with the prior art is shown, for example, by the compound according to preparation Example 5.

It is understood that the specification and examples are illustrative but not limitative of the present invention and that other embodiments within the spirit and scope of the invention will suggest themselves to those skilled in the art.

We claim:

1. An E-isomer of an $N^{\alpha}$-(s-cyano-2-alkoximinoacetyl)amino acid derivative or peptide of the formula

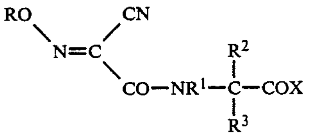

in which

R represents alkyl, alkenyl, alkinyl, cyanoalkyl, azolylalkyl or optionally substituted phenylalkyl, or represents optionally substituted cycloalkyl;

$R^1$ represents hydrogen, alkyl, optionally substituted phenyl or optionally substituted benzyl, or represents alkoxycarbonylamino;

$R^2$ represents hydrogen or alkyl;

$R^3$ represents hydrogen, alkyl, alkoxycarbonylalkyl, hydroxycarbonylalkyl, aminocarbonylalkyl, azolylalkyl, cyanoalkyl, hydroxyalkyl, alkenyl, alkinyl or optionally substituted cycloalkyl, or represents optionally substituted phenyl or phenylalkyl, or represents the grouping $R^4$—$SO_n$—Z— wherein $R^4$ represents hydrogen, alkyl or optionally substituted phenylalkyl;

n represents the numbers 0, 1 or 2 and

Z represents a straight-chain or branched alkylene chain; or $R^1$ and $R^3$, together with the nitrogen atom and the carbon atom to which they are bonded, represent a 5- or 6-membered heterocyclic ring; or $R^2$ and $R^3$, together with the carbon atom to which they are bonded, represent cycloalkylidene and X represents the grouping $—OR^I$ or $NR^{II}R^{III}$, wherein $R^I$ represents hydrogen, alkyl or alkenyl, or represents alkinyl;

$R^{II}$ represents hydrogen or alkyl;

$R^{III}$ represents hydrogen, alkyl, alkenyl, alkinyl, halogenoalkyl, alkoxyalkyl, dialkylaminoalkyl, alkoxycarbonylalkyl, hydroxycarbonylalkyl, aminocarbonylalkyl, alkylaminocarbonylalkyl, dialkylaminocarbonylalkyl, cyanoalkyl, optionally substituted phenylalkyl, optionally substituted phenyl or optionally substituted cycloalkyl, or represents an acylamino radical, or represents the grouping $$—N{=}CH—R^{IV}$$

wherein $R^{IV}$ represents alkyl or optionally substituted phenyl, or $R^{II}$ and $R^{III}$, together with the nitrogen atom to which they are bonded, represent an optionally substituted heterocyclic ring, which can contain further hetero atoms, or an optionally substituted ammonium, alkali metal or alkaline earth metal salt or metal salt complex thereof.

2. An E-isomer, salt or complex according to claim 1, in which

R represents straight-chain or branched alkyl with 1 to 8 carbon atoms or alkenyl or alkinyl with in each case 2 to 4 carbon atoms, cyanoalkyl with 1 to 4 carbon atoms, 1,2,4-triazol-1-yl-alkyl or pyrazol-1-yl-alkyl with 1 to 6 carbon atoms in the alkyl part in each case, or represents phenylalkyl which has 1 to 4 carbon atoms in the alkyl part and is optionally mono-, di- or trisubstituted in the phenyl part by identical or different substituents, selected from the group consisting of halogen, cyano, nitro, hydroxyl, alkyl, alkoxy, alkylthio, alkylsulfinyl and alkylsulfonyl with in each case 1 to 4 carbon atoms and phenyl which is optionally mono-, di- or trisubstituted by identical or different halogen substituents; or represents cycloalkyl which has 3 to 7 carbon atoms and is optionally mono-, di- or trisubstituted by identical or different substituents, selected from the group consisting of halogen and alkyl with 1 to 4 carbon atoms;

$R^1$ represents hydrogen or straight-chain or branched alkyl with 1 to 4 carbon atoms, or represents phenyl or benzyl, in each case optionally mono-, di- or trisubstituted by identical or different substituents selected from phenyl substituents already mentioned for R, or represents alkoxycarbonylamino with 1 to 4 carbon atoms in the alkyl part, $R^2$ represents hydrogen or straight-chain or branched alkly with 1 to 4 carbon atoms;

$R^3$ represents hydrogen or straight-chain or branched alkyl with 1 to 6 carbon atoms, or represents straight-chain or branched hydroxyalkyl with 1 to 4 carbon atoms, alkoxycarbonylalkyl with 1 to 4 carbon atoms in each alkyl part and alkoxy part respectively, hydroxycarbonylalkyl and aminocarbonylalkyl with 1 to 4 carbon atoms in each alkyl part, 1,2,4-triazol-1-yl-alkyl, 1,2,4-triazolyl-4-yl-alkyl, imidazol-4-yl-alkyl and pyrazol-1-yl-alkyl with 1 to 6 carbon atoms in the alkyl part in each case, cyanoalkyl with 1 to 4 carbon atoms in the alkyl part, or represents alkenyl or alkinyl with in each case 2 to 4 carbon atoms, or represents cycloalkyl which has 3 to 7 carbon atoms and is optionally mono-, di- or trisubstituted by identical or different substituents selected from the group consisting of halogen and alkyl with 1 to 4 carbon atoms, or furthermore represents phenyl or phenyalkyl, with 1 to 4 carbon atoms in the alkyl part, optionally mono-, di- or trisubstituted in the phenyl part by identical or different substituents, selected from the phenyl substituents already mentioned for R, or represents the grouping $$R^4—SO_n—Z—$$

wherein $R^4$ represents hydrogen, or represents straight-chain or branched alkyl with 1 to 4 carbon atoms, or represents phenylalkyl which has 1 to 4 carbon atoms in the alkyl part and is optionally mono-, di- or trisubstituted in the phenyl part by identical or different substituents selected from the phenyl substituents already mentioned for R, n represents the number 0, 1 or 2 and Z represents a straight-chain or branched alkylene chain with 1 to 4 carbon atoms; or $R^1$ and $R^3$, together with the nitrogen atom and the cargon atom to which they are bonded, represent a 5- or 6-membered heterocyclic ring; or $R^2$ and $R^3$, together with the carbon atom to which they are bonded, represent cycloalkylidene with 3 to 6 carbon atoms;

X represents the groupings $—OR^I$ or $—NR^{II}R^{III}$, wherein $R^I$ represents hydrogen or straight-chain or branched alkyl with 1 to 4 carbon atoms or alkenyl or alkinyl with in each case 2 to 4 carbon atoms;

$R^{II}$ represents hydrogen or straight-chain or branched alkyl with 1 to 4 carbon atoms; and $R^{III}$ represents hydrogen or straight-chain or branched alkyl with 1 to 4 carbon atoms, or represents alkenyl or alkinyl with in each case 2 to 4 carbon atoms, or halogenoalkyl with 1 to 4 carbon atoms and 1 to 5 same or different halogen atoms, or alkoxyalkyl with 1 to 4 carbon atoms in the alkoxy and in the alkyl part, or dialkylaminoalkyl with up to 4 carbon atoms in each alkyl part, or represents alkoxycarbonylalkyl with in each case 1 to 4 carbon atoms in the alkoxy part and in the alkyl part, hydroxycarbonylalkyl with 1 to 4 carbon atoms in the alkyl part or aminocarbonylalkyl, alkylaminocarbonylalkyl or dialkylaminocarbonylalkyl with in each case 1 to 4 carbon atoms in each alkyl part or represents cyanoalkyl with 1 to 4 carbon atoms in the alkyl part, phenylalkyl which has 1 to 4 carbon atoms in the alkyl part and is optionally mono-, di- or trisubstituted in the phenyl part by identical or different substituents or phenyl which is mono-, di- or trisubstituted by identical or different substituents, the substituents in each case being the phenyl substituents already mentioned for R, or represents cycloalkyl which has 3 to 7 carbon atoms and is optionally substituted by identical or different substituents selected from the group consisting of halogen and alkyl with 1 to 4 carbon atoms, or represents alkylcarbonylamino or alkoxycarbonylamino with in each case 1 to 4 carbon atoms in the alkyl part or in the alkoxy part, or furthermore represents aminocarbonylamino, alkylaminocarbonylamino or dialkylaminocarbonylamino with 1 to 4 carbon atoms in each alkyl part and in each case, or formylamino, or represents the grouping

—N=CH—$R^{IV}$ $R^{IV}$ represents straight-chain or branched alkyl with 1 to 4 carbon atoms or phenyl which is optionally mono-, di or trisubstituted by identical or different substituents, the substituents being the phenyl substituents already mentioned for R, or $R^{II}$ and $R^{III}$, together with the nitrogen atom to which they are bonded, represent a 5- or 6-membered heterocyclic ring, which can optionally contain oxygen or nitrogen as further hetero atoms and can optionally be substituted by cyano, halogen, alkyl with 1 to 4 carbon atoms, hydroxycarbonyl, alkoxycarbonyl with 1 to 4 carbon atoms in the alkoxy part, aminocarbonyl, alkylaminocarbonyl and dialkylaminocarbonyl with 1 to 4 carbon atoms in each alkyl part in each case.

3. An E-isomer, salt or complex according to claim 1, wherein

R represents straight-chain or branched alkyl with 1 to 4 carbon atoms, allyl or propargyl, cyanomethyl, cyanoethyl, 1,2,4-triazol-1-yl-alkyl or pyrazol-1-yl-alkyl with 1 to 4 carbon atoms in the alkyl part in each case, or represents phenylalkyl which has 1 to 2 carbon atoms in the alkyl part and is optionally mono- or disubstituted in the phenyl part by identical or different substituents selected from the group consisting of fluorine, chlorine, cyano, nitro, hydroxyl, methyl, methoxy, methylthio, methylsulfinyl, methylsulfonyl and phenyl which is optionally mono- or disubstituted by identical or different substituents from the group consisting of fluorine and chlorine; or furthermore represents cyclopropyl, cyclobutyl, cyclopentyl, cyclohexyl or cycloheptyl, in each case optionally mono- or disubstituted by identical or different substituents from the group consisting of fluorine, chlorine or methyl;

$R^1$ represents hydrogen, methyl or ethyl, or represents phenyl or benzyl, in each case optionally mono- or disubstituted by identical or different substituents, the substituents being the phenyl substituents already mentioned for R; or furthermore represents methoxycarbonylamino or ethoxycarbonylamino;

$R^2$ represents hydrogen, methyl or ethyl;

$R^3$ represents hydrogen, straight-chain or branched alkyl with 1 to 4 carbon atoms, hydroxymethyl or 1-hydroxyethyl, methoxycarbonylmethyl, methoxycarbonylethyl, ethoxycarbonylmethyl, ethoxycarbonylethyl, hydroxycarbonylmethyl, hydroxycarbonylethyl, aminocarbonylmethyl, aminocarbonylethyl, 1,2,4-triazol-1-yl-alkyl, 1,2,4-triazol-4-yl-alkyl, imidazol-4-yl-alkyl and pyrazol-1-yl-alkyl with 1 to 4 carbon atoms in each alkyl part in each case, cyanomethyl, cyanoethyl, or represents allyl, or represents propargyl, or represents cyclopropyl, cyclobutyl, cyclopentyl, cyclohexyl or cycloheptyl, in each case optionally mono- or disubstituted by identical or different substituents from the group consisting of fluorine, chlorine and methyl; or furthermore represents phenylalkyl which has 1 to 2 carbon atoms in the alkyl part and is optionally mono- or disubstituted in the phenyl part by identical or different substituents, or phenyl which is mono- or disubstituted by identical or different substituents, the substituents being the phenyl substituents already mentioned for R, or furthermore represents the grouping $R^4$—$SO_n$—Z— wherein $R^4$ represents hydrogen, methyl or ethyl, or represents phenylalkyl which has 1 to 2 carbon atoms in the alkyl part and is optionally mono- or disubstituted in the phenyl part by idential or different substituents, the substituents being the phenyl substituents already mentioned for R, n represents the number 0, 1 or 2 and Z represents a straight-chain or branched alkylene chain with 1 or 2 carbon atoms; or $R^1$ and $R^3$, together with the nitrogen atom and the carbon atom to which they are bonded, represents a 5- to 6-membered heterocyclic ring;

$R^2$ and $R^3$, together with the carbon atom to which they are bonded, represent cyclopropylidene, and X represents the groupings —$OR^I$ or —$NR^{II}R^{III}$, wherein $R^I$ represent hydrogen, methyl, ethyl, allyl or propargyl;

$R^{II}$ represents hydrogen, methyl or ethyl;

$R^{III}$ represents hydrogen, methyl, ethyl, n-propyl, isopropyl, n-butyl, sec.-butyl, tert.-butyl, allyl or propargyl, halogenoalkyl with 1 or 2 carbon atoms and 1 to 3 same or different halogen atoms, alkoxyalkyl with each 1 or 2 carbon atoms in the alkoxy and alkyl part, dialkylaminoalkyl with 1 or 2 carbon atoms in each alkyl part, or represents alkoxycarbonylalkyl, hydroxycarbonylalkyl, aminocarbonylalkyl, alkylaminocarbonylalkyl or dialkylaminocarbonylalkyl with in each case 1 or 2 carbon atoms in each alkyl part, or cyanoalkyl with 1 or 2 carbon atoms in the alkyl part or furthermore represents phenylalkyl which has 1 or 2 carbon atoms in the alkyl part and is optionally mono- or disubstituted in the phenyl part by identical or different substituents or represents phenyl which-is mono- or disubstituted by identical or different substituents, the substituents being in each case the phenyl substituents already mentioned for R; or represents cyclopropyl, cyclobutyl, cyclopentyl, cyclohexyl or cycloheptyl, in each case optionally mono- or disubstituted by identical or different substituents from the group consisting of fluorine, chlorine and methyl, or represents alkylcarbonylamino or alkoxycarbonylamino with in each case 1 or 2 carbon atoms in the alkyl part or in the alkoxy part, or represents aminocarbonylamino, methylaminocarbonylamino, ethylaminocarbonylamino, dimethylaminocarbonylamino, diethylaminocarbonylamino, methylethylaminocarbonylamino or formylamino, or represents the grouping

—N=CH—$R^{IV}$ wherein $R^{IV}$ represents methyl or ethyl, or represents phenyl which is optionally mono- or idsubstituted by identical or different substituents, the substituents being the phenyl substituents already mentioned for R; or $R^{II}$ and $R^{III}$, together with the nitrogen atom to which they are bonded, represent a 5- or 6-membered heterocyclic ring, which can optionally contain oxygen or nitrogen as further hetero atoms and can optionally substituted by cyano, fluor, chlor, brom, jod, methyl, ethyl, i-propyl, hydroxycarbonyl, methoxycarbonyl, ethoxycarbonyl, aminocarbonyl, methylaminocarbonyl, ethylaminocarbonyl, dimethylaminocarbonyl, diethylaminocarbonyl and methylethylaminocarbonyl.

4. An E-isomer according to claim 1, wherein such compound is $N^{\alpha}$-(2-cyano-2-methoximino-acetyl)-glycine benzylamide of the formula

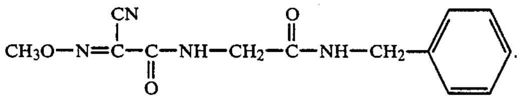

5. An E-isomer according to claim 1, wherein such compound is $N^{\alpha}$-(2-methoximino-2-cyano-acetyl)-glycine N,N-diethylamide of the formula

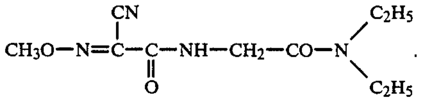

6. An E-isomer according to claim 1, wherein such compound is $N^{\alpha}$-(2-cyano-2-methoximino-acetyl)-glycine cyclohexylamide of the formula

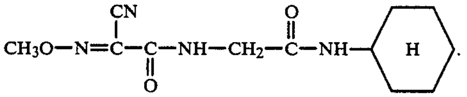

7. An E-isomer according to claim 1, wherein such compound is $N^{\alpha}$-(2-cyano-2-methoximino-acetyl)-glycine phenylamide of the formula

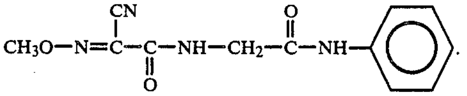

8. An E-isomer according to claim 1, wherein such compound is $N^{\alpha}$-(2-cyano-2-methoximino-acetyl)-glycine 2-chlorophenylamide of the formula

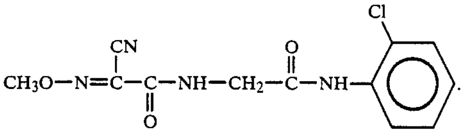

9. An E-isomer according to claim 1, wherein such compound is $N^{\alpha}$-(2-cyano-2-cyanomethoximino-acetyl)-glycine diethylaminocarbonylmethylamide of the formula

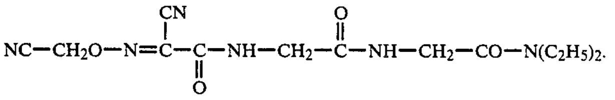

10. An E-isomer according to claim 1, wherein such compound is $N^{\alpha}$-(2-cyano-2-methoximino-acetyl)-glycine phenethylamide of the formula

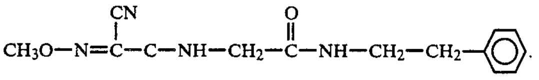

11. A fungicidal composition comprising a fungicidally effective amount of a compound, salt or metal salt complex according to claim 1 and a diluent.

12. A method of combating fungi which comprises applying to such fungi or to a fungus habitat a fungicidally effective amount of a compound, salt or metal salt complex according to claim 1.

13. A method according to claim 12 wherein such compound is $N^{\alpha}$-(2-cyano-2-methoximino-acetyl)-glycine benzylamide, $N^{\alpha}$-(2-methoximino-2-cyano-acetyl)-glycine N,N-diethylamide, $N^{\alpha}$-(2-cyano-2-methoximino-acetyl)-glycine cyclohexylamide, $N^{\alpha}$-(2-cyano-2-methoximino-acetyl)-glycine phenylamide, $N^{\alpha}$-(2-cyano-2-methoximino-acetyl)-glycine 2-chlorophenylamide, $N^{\alpha}$-(2-cyano-2-cyanomethoximino-acetyl)-glycine diethylaminocarbonylmethylamide, or $N^{\alpha}$-(2-cyano-2-methoximino-acetyl)-glycine phenethylamide.

* * * * *

UNITED STATES PATENT AND TRADEMARK OFFICE

CERTIFICATE OF CORRECTION

PATENT NO. : 4,782,086

DATED : November 1, 1988

INVENTOR(S) : Winfried Lunkenheimer, et al

It is certified that error appears in the above-identified patent and that said Letters Patent is hereby corrected as shown below:

| | |
|---|---|
| Col. 1, line 45 and Col. 2, line 35 | Correct --substituted-- |
| Col. 5, line 9 | After "identical" insert --or-- |
| Col. 5, line 12 and Col. 8, line 32 | Correct spelling of --substituents-- |
| Col. 7, line 29 | Before "cyclopropyl" delete "or" |
| Col. 8, line 39 | Before "substituted" insert --be-- |
| Col. 11, line 37 | Delete "G," and substitute --G.-- |
| Col. 12, line 13 | Correct --definition of-- |
| Col. 12, line 17 | Correct --atoms-- |
| Col. 12, line 64 | Delete "agent" and substitute --agents-- |
| Col. 16, line 31 | After "dressing" insert --,-- |
| Col. 17, line 52 | Correct --suspended-- |
| Col. 20, line 32 | Delete "Substances" and substitute --Substance-- |
| Col. 24, last column, last line | Delete "1,5223" and substitute --1.5223-- |
| Col. 26, last column, last line | Delete "136-140°C" and substitute --135-140°C-- |
| Col. 49, line 55 | Before "phenyl" insert --the-- |
| Col. 49, line 59 | Correct --alkyl-- |
| Col. 50, line 29 | Delete "cargon" and substitute --carbon-- |
| Col. 51, line 41 | Before "methyl" delete "or" and substitute --and-- |
| Col. 52, line 10 | Correct --identical-- |

UNITED STATES PATENT AND TRADEMARK OFFICE

CERTIFICATE OF CORRECTION

PATENT NO. : 4,782,086

DATED : November 1, 1988

INVENTOR(S) : Winfried Lunkenheimer, et al

It is certified that error appears in the above-identified patent and that said Letters Patent is hereby corrected as shown below:

| | |
|---|---|
| Col. 52, line 61 | Correct --disubstituted-- |
| Col. 52, line 68-69 | Delete "fluor, chlor, brom, jod" and substitute --fluoro, chloro, bromo, iodine-- |

Signed and Sealed this

Nineteenth Day of September, 1989

Attest:

DONALD J. QUIGG

Attesting Officer

Commissioner of Patents and Trademarks